United States Patent [19]

Oguma et al.

[11] Patent Number: 5,364,936
[45] Date of Patent: Nov. 15, 1994

[54] CYCLOISOMALTOOLIGOSACCHARIDES

[75] Inventors: Tetsuya Oguma; Tatsuo Horiuchi; Koichiro Tobe, all of Noda, Japan

[73] Assignees: Kikkoman Corporation; Noda Institute for Scientific Research, Chiba, Japan

[21] Appl. No.: 174,596

[22] Filed: Dec. 28, 1993

[30] Foreign Application Priority Data

Dec. 28, 1992 [JP] Japan .................................. 4-349444
Jun. 24, 1993 [JP] Japan .................................. 5-153456

[51] Int. Cl.$^5$ ........................ C08B 37/16; C08B 37/02
[52] U.S. Cl. .................................. 536/103; 536/112; 536/123.1; 536/123.12
[58] Field of Search .................... 536/103, 112, 123.1, 536/123.12

[56] References Cited

U.S. PATENT DOCUMENTS 4,135,977 1/1979 Kenkyusho .

FOREIGN PATENT DOCUMENTS 29750 10/1949 Luxembourg .

OTHER PUBLICATIONS

Sundari et al, "Hydrophobic surfaces in oligosaccharides: linear dextrins are amphiphilic chains," Bioch. Biophys. Acta: 1065:35–41 (1991).
Shiraishi et al, "Synthesis of Maltosyl($\alpha$1–6)cyclodextrins . . . " Agric. Biol. Chem. 53(8):2181–2188 (1989).

Primary Examiner—Douglas W. Robinson
Assistant Examiner—Francisco C. Prats
Attorney, Agent, or Firm—Pennie & Edmonds

[57] ABSTRACT

The present invention relates to a novel cycloisomaltooligosaccharide selected from the group consisting of novel cycloisomaltoheptaose having a cyclic structure composed of 7 glucose residues in $\alpha$-1,6 linkage, novel cycloisomaltooctaose having a cyclic structure composed of 8 glucose residues in $\alpha$-1,6 linkage and novel cycloisomaltononaose having a cyclic structure composed of 9 glucose residues in $\alpha$-1,6 linkage, novel cycloisomaltooligosaccharide synthase forming said oligosaccharides from dextran, and a process for producing said oligosaccharides by use of said enzyme or a microorganism capable of producing said enzyme.

4 Claims, 4 Drawing Sheets

F₁: Cycloisomaltoheptaose   IG₆: Isomaltohexaose
F₂: Cycloisomaltooctaose    IG₇: Isomaltoheptaose
F₃: Cycloisomaltononaose    G  : Glucose F1: Cycloisomaltoheptaose
F2: Cycloisomaltooctaose
F3: Cycloisomaltononaose 1. Cycloisomaltoheptaose
2. Cycloisomaltooctaose
3. Cycloisomaltononaose

CYCLOISOMALTOOLIGOSACCHARIDES

BACKGROUND OF THE INVENTION

1. Field of the Invention

The present invention relates to novel isomaltooligosaccharides, novel isomaltooligosaccharide synthase forming said oligosaccharides from dextran, and a process for producing said oligosaccharides by using said enzyme or a microorganism capable of producing said enzyme.

2. Description of the Prior Art

Conventionally, a cyclodextrin of 6–8 glucose residues bound by α-1,4 linkages is well known among cyclooligosaccharides. The cyclodextrin, owing to its hydrophobicity in the center of the ring, possesses the ability (inclusion ability) to bind to a variety of hydrophobic substances. For this property, the compound has been applied and developed for stabilization and improvements in solubility etc. of various substance in a wide range of fields such as medicaments, cosmetics, foods, etc. (Handbook of Amylases and Related Enzymes, pp. 233–243 (1988), compiled by Japanese Amylase Research Society.

In recent years, cyclooligosaccharides consisting of 6–8 fructose residues in α-2,1 linkage have also been found which, similar to the cyclodextrin, are expected to be applied to a wide range of fields (Carbohyd. Res., vol. 192, pp. 83–90 (1989)).

In addition to the aforementioned saccharides, a wide variety of cyclooligosaccharides, such as cyclosophoraose composed of 17–24 glucose residues in α-1,2 linkage, cyclogentiooligosaccharides of 3–4 glucose residues in α-1,6 linkage, cycloawaodorin with 6 rhamnose molecules cyclized, cyclomannohexaose with 6 mannose molecules cyclized, etc., have been enzymatically or chemically synthesized.

However, none of the cyclooligosaccharides of glucose residues bound by α-1,6 linkages have been known so far.

OBJECTS AND SUMMARY OF THE INVENTION

The object of the present invention is to provide novel cycloisomaltooligosaccharides of glucoses bound by α-1,6 linkages expected highly useful, a process for producing the same, novel cycloisomaltooligosaccharide synthase forming said oligosaccharides from dextran, and a process for producing said enzyme.

As a result of screening from soil a microorganism forming cyclooligosaccharides from dextran, the present inventors found that a bacterial strain belonging to the genus Bacillus produces novel cyclooligosaccharides and novel cycloisomaltooligosaccharide synthase.

That is, the present invention encompasses:

(1) A novel cycloisomaltooligosaccharide selected from the group consisting of novel cycloisomaltoheptaose with a cyclic structure composed of 7 glucose residues in α-1,6 linkage, novel cycloisomaltooctaose with a cyclic structure composed of 8 glucose residues in α-1,6 linkage and novel cycloisomaltononaose with a cyclic structure composed of 9 glucose residues in α-1,6 linkage.

(2) The cycloisomaltooligosaccharide according to item (1), represented by formula (I):

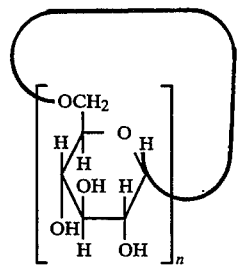

wherein n stands for an integer of 7–9.

(3) The novel cycloisomaltooligosaccharide according to item (2), wherein n is 7.

(4) The novel cycloisomaltooligosaccharide according to item (2), wherein n is 8.

(5) The novel cycloisomaltooligosaccharide according to item (2), wherein n is 9.

(6) Novel cycloisomaltooligosaccharide synthase, having the physicochemical properties of:

① action on a polymer of glucoses linked by α-1,6 linkages such as dextran etc. to form a cycloisomaltooligosaccharide by intramolecular transglucosylation reaction;

② substrate specificity of acting on dextran having an α-1,6 linkage as a main chain, but not on amylopectin, pullulan, etc., having an α-1,6 linkage of glucoses only partially in the structure; and ③ optimum pH in the vicinity of pH 5.5 and stability pH in the range of pH 4.5–8.5.

(7) A process for producing novel cycloisomaltooligosaccharide synthase, which comprises culturing in a dextran-containing medium a microorganism belonging to the genus Bacillus capable of producing the enzyme of item (6), and then recovering said enzyme from the culture.

(8) A process for producing cycloisomaltooligosaccharides, which comprises allowing the enzyme of item (6) to act on dextran in order to form cycloisomaltooligosaccharides.

(9) A process for producing cycloisomaltooligosaccharides, which comprises allowing a microorganism-free mixture obtained by culturing in a dextran-containing medium a microorganism belonging to the genus Bacillus capable of producing the enzyme of item (6) to act on dextran in order to form cycloisomaltooligosaccharides.

(10) A process for producing cycloisomaltooligosaccharides, which comprises culturing in an α-1,6 glucan-containing medium a microorganism belonging to the genus Bacillus capable of producing the cycloisomaltooligosaccharide of item (1), and then recovering said cycloisomaltooligosaccharide from the culture.

Hereinafter, the present invention is described in detail.

We will first describe the physicochemical properties of novel cycloisomaltooligosaccharides (cycloisomaltoheptaose, cycloisomaltooctaose and cycloisomaltononaose)and next identify them as cyclooligosaccharides on the basis of the properties.

1. Elementary analysis revealed that the present compounds are cyclic heptamer, octamer and nonamer of glucoses, respectively, as is evidenced by the following data:

Cycloisomaltoheptaose (as $C_{42}H_{70}O_{35}.3H_2O$)
Calculated; C: 42.43 % H: 6.44 %
Determined; C: 42.78 % H: 6.33 %
Cycloisomaltooctaose (as $C_{48}H_{80}O_{40}.4H_2O$)
Calculated; C: 42.11% H: 6.48 %
Determined; C: 42.37 % H: 6.24 %
Cycloisomaltononaose (as $C_4H_9O_{45}.5H_2O$)
Calculated; C: 41.86 % H: 6.51%
Determined: C: 41.53 % H: 6.18 %

2. Mass spectral analysis gave the following molecular weights (determined with mass spectrometer 80B manufactured by Hitachi Seisakusho Co., Ltd.):
Cycloisomaltoheptaose; 1134
Cycloisomaltooctaose; 1296
Cycloisomaltononaose; 1458
The results agree with the molecular weights estimated from their molecular formulae.

3. The definite melting points of the present compounds could not be determined in a melting point measuring instrument manufactured by Yanagimoto Co., Ltd. Their discoloration temperature ranges together with decomposition temperatures are as follows:
Cycloisomaltoheptaose; 234°–238° C.
Cycloisomaltooctaose; 238°–241° C.
Cycloisomaltononaose; 239–242° C.

4. Their ultraviolet absorption spectra did not show any characteristic absorption (taken with Spectrophotometer 775 manufactured by Hitachi Seisakusho Co., Ltd.). This result suggested the absence of such functional group as amino, carboxyl, etc.

5. FIG. 1 shows their infrared absorption spectra recorded with IR spectrum meter model FT/IR-7300 manufactured by Nihon Bunko Co., Ltd. Cyclic heptamer, octamer, and nonamer of glucoses are shown respectively in FIG. 1A, B and C where absorption peaks are present at $917\pm2$ cm$^{-1}$ and $768\pm1$ cm$^{-1}$ characteristic of $\alpha$-1,6 linkage, indicating the presence of $\alpha$-1,6 linkages in the oligosaccharides.

6. The solubilities of the oligosaccharides in solvent are at least 20 mg/l at room temperature.

7. The Somogyi-Nelson method strongly suggested the absence of any reducing terminal in the oligosaccharides.

8. The present compounds are white substances of neutral pH.

9. Their cyclic structure was supported in $^{13}$C-NMR by the presence of only 6 signals recorded with NMR spectrometer model NM-FX200 manufactured by Nihon Denshi Co., Ltd. Analysis of the isomaltoheptaose strongly suggested $\alpha$-1,6 linkage as linkage type.
The present compounds were enzymatically analyzed as follows:

10. Glucodextranase, i.e. exo-type dextranase, was allowed to act on the present compounds (1% solution), but they were not hydrolyzed at all as shown in FIG. 2. Under the same conditions, isomaltohexaose and isomaltoheptaose were completely hydrolyzed. This result suggests that the present compounds are not linear isomaltooligosaccharides.

11. The present compounds (1% solution) were decomposed to glucose and isomaltose with endo-type dextranase. This suggests that the present compounds (oligosaccharides) are composed exclusively of glucose residues as constituent units bound via $\alpha$-1,6 linkages.

It was evidenced by the results of items 1 to 11 above that the present compounds are cyclooligosaccharides of 7–8 glucose residues bound by $\alpha$-1,6 linkages. The chemical structure of the cycloisomaltooligosaccharides is represented by formula (I):

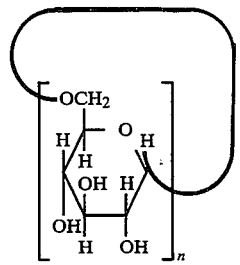

wherein n stands for an integer of 7–9.

As explained above in detail, the present cyclooligosaccharides differ completely from conventional cyclooligosaccharides in respect of the properties, and are completely new in that they consist of glucoses bound by $\alpha$-1,6 linkages. Owing to their cyclic structure, the present compounds have an inclusion ability useful for stabilization, solubilization, etc., of substances of different size not covered by cyclodextrin, and they are used specifically as inclusion agents for medicaments, foods, etc.

The present novel cycloisomaltooligosaccharide synthase has the enzymatic chemical properties of:

① action on a polymer of glucoses bound by $\alpha$-1,6 linkages such as dextran etc. to form a cycloisomaltooligosaccharide by intramolecular transglucosylation reaction;

② substrate specificity of acting on dextran having an $\alpha$-1,6 linkage as a main chain, but not on amylopectin, pullulan, etc., having an $\alpha$-1,6 linkage of glucoses only partially in the molecule; and ③ optimum pH in the vicinity of pH 5.5 and stability pH in the range of pH 4.5–8.5.

As described in detail above, the present enzyme differs in the properties from conventional cyclooligosaccharide synthases, cyclodextrin glucanotransferase (referred to hereinafter as "CGTase"; EC 2.4.1.19), cycloinulooligosaccharide synthase (referred to hereinafter as "CFTase") and cyclic $\alpha$-1,2 glucan synthetase, and the present enzyme is novel in that it forms from dextran a cyclooligosaccharide of glucoses bound by $\alpha$-1,6 linkages. Like CGTase and CFTase, the present enzyme is a multifunctional enzyme which, besides intramolecular transglucosylation reaction, catalyzes the reaction (coupling reaction) of forming an isomaltooligosaccharide having an OH acceptor bound thereto by intermolecular transglucosylation reaction of a cycloisomaltooligosaccharide and a suitable acceptor, as well as the reaction (disproportionation reaction) of forming isomaltooligosaccharides of various polymerization degrees from isomaltooligosaccharides.

Hereinafter, a process for producing the enzyme of the present invention is described.

The microorganism used in the present invention may be any of the microorganisms belonging to the genus Bacillus capable of forming cycloisomaltooligosaccharide synthase, and an example is Bacillus sp. T-3040 or the like. Bacillus sp. T-3040 is a wild strain obtained by screening from soil, and possesses the following bacterial properties:

| (1) morphological features | |
| --- | --- |
| 1. form | Bacillus |
| 2. motility | recognizable |
| 3. spore | present |
| sporangium position | evagination (central or subterminal) |
| 4. Gram stainability | + |

| (2) growth states | |
| --- | --- |
| 1. meat agar plate culture | smooth and no pigment occurrence |
| 2. meat agar slant culture | smooth and no pigment occurrence |

| (3) physiological properties | | |
| --- | --- | --- |
| 1. nitrate reduction | − | |
| 2. denitrification | − | |
| 3. MR test | − | |
| 4. VP test | − | |
| 5. indole formation | − | |
| 6. hydrogen sulfide formation | − | |
| 7. starch hydrolysis | + | |
| 8. citric acid utilization | − | |
| 9. utilization of inorganic nitrogen sources | | |
| nitrate | − | |
| ammonium salt | + | |
| 10. urease | − | |
| 11. oxidase | − | |
| 12. catalase | + | |
| 13. growth temperature range | 10–37° C. | |
| 14. attitude toward oxygen | aerobic | |
| 15. O-F test | − | |
| 16. attitude toward sugars | acid formation | gas formation |
| (1) L-arabinose | + | − |
| (2) D-xylose | − | − |
| (3) D-glucose | + | − |
| (4) D-mannose | − | − |
| (5) D-fructose | − | − |
| (6) D-galactose | + | − |
| (7) maltose | + | − |
| (8) sucrose | + | − |
| (9) lactose | + | − |
| (10) trehalose | + | − |
| (11) D-sorbitol | − | − |
| (12) D-mannitol | − | − |
| (13) inositol | − | − |
| (14) glycerin | − | − |
| (15) starch | + | − |

The bacterial strain T-3040 is a spore-forming Gram-positive microorganism, and the present inventors have identified it as a microorganism belonging to the genus Bacillus, but they could not identified its species in spite of extensive identification on the basis of Bergey's Manual of Systematic Bacteriology, vol. 2. This microorganism, identified merely as a bacterial strain belonging to the genus Bacillus, is designated *Bacillus* sp. T-3040 and has been deposited with Fermentation Research Institute currently National Institute of Bioscience and Human Technology, Agency of Industrial Science and Technology 1-3, Higashi-1-Chome, Tsukuba-shi, Ibaraki-ken 305, Japan under FERMBP-4132 on Dec. 25, 1992.

The microorganism according to the present invention is aerobically cultured in the same manner as for conventional microorganisms, usually shake culture in liquid medium, spinner culture under aeration, etc. The medium used is composed e.g. of a suitable nitrogen source (e.g., casein hydrolyzates such as peptone, polypeptone, bactotrypton, etc., or soy bean protein hydrolyzates such as soytone etc.), carbon source (e.g. sugar contents such as glucose, glycerin, etc.), and as necessary, yeast extract, vitamins such as riboflavin etc. and phosphates, magnesium salt, sodium chloride, minerals e.g. trace metals, and dextran etc. serving as starting materials for the present cycloisomaltooligosaccharides. The pH of the medium may be in any pH range in which the present microorganism can grow, preferably at pH 6–8.

The microorganism is cultured e.g. under shaking or stirring under aeration, usually at 20°–40° C., preferably 30° C. and for 16 hours—6 days, preferably 3 days.

The present cyclooligosaccharide synthase is obtained from the resulting culture, for example, according to the following enzyme purification step. A microorganism-free enzyme preparation produced merely by centrifuging the culture and then concentrating the resulting supernatant through a membrane can be used for the production of the present cyclooligosaccharides, and as necessary, a purified standard is obtained in a usual manner from this crude enzyme preparation.

Any of the conventional purification method can be used for the present enzyme. A cyclooligosaccharide synthase standard of high purity can be obtained by treating a microorganism-free culture as described below.

Then, the present enzyme is allowed to act on dextran for production of cycloisomaltooligosaccharides.

The enzyme reaction is effected at 10°–60° C., preferably 40° C., at pH 4.5–8.0, preferably 5.0–6.5 and for 10–72 hours, preferably 48 hours. As necessary, the reaction solution may be stirred and an organic solvent such as methanol, ethanol, etc., may be added to the reaction solution. In the present process, the cycloisomaltooligosaccharides can be formed by use of the aforementioned microorganism-free concentrate of the culture in the same efficiency as attained by use of the purified enzyme. Any purification method for conventional oligosaccharides can also be employed as the means of obtaining the present oligosaccharides from the reaction solution. Methods known to the art, such as cooling, treatment with organic solvent or active carbon, chromatography on an active carbon column or cyclooligosaccharide-specific adsorption column, etc., may be used singly or in combination.

The cycloisomaltooligosaccharides of the present invention can also be obtained by e.g. the recovering step as described below from a culture of said microorganism in a medium containing α-1,6 glucan such as dextran etc.

The culture is centrifuged for removal of the microorganisms, and then concentrated through a membrane. The microorganism-free concentrate thus obtained is subjected to a purification method for conventional cyclodextrin, to give high-purity cyclooligosaccharide fractions.

A high-purity sample of each cyclooligosaccharide can be obtained by a purification means such as high performance liquid chromatography (HPLC) on a partition-adsorption column etc. Conventional methods such as cooling, treatment with organic solvent or activated charcoal, chromatography on an activated charcoal column or cyclooligosaccharide-specific adsorption column, etc., may be used singly or in combination for purification of the cycloisomaltooligosacchrides from the microorganism-free culture concentrate.

According to the present invention, there can be provided novel cycloisomaltooligosaccharides composed of glucose residues bound by α-1,6 linkage useful as inclusion agents for medicaments, foods, etc., and a process for producing said oligosaccharides of high purity in high yield by using a microorganism belonging to the genus Bacillus. Furthermore, according to the present invention, there can also be provided novel cycloisomaltooligosaccharise synthase allowing said cycloisomaltooligosaccharides to be efficiently produced in high yield in a very simple procedure. Hence, the present invention is extremely useful in industry.

DESCRIPTION OF THE PREFERRED EMBODIMENTS

The present invention is described in more detail with reference to the following examples, which however are not intended to limit the scope of the present invention.

EXAMPLE 1

3 ml of a liquid medium (tap water, pH 7.0) composed of 1% dextran T2000, 1% peptone, 0.5 % NaCl and 0.1% yeast extract was put in 15 ml test tube and then sterilized at 120° C. for 20 min. The microorganism, *Bacillus* sp. T-3040 (FERM BP-4132), was inoculated onto the medium and cultured at 30° C. for 1 day under shaking. Subsequently, the culture solution, 3 ml, was inoculated onto 2 l medium in 3 l mini-jar with the same medium composition sterilized under the same conditions as described above, and the microorganism was aerobically cultured at 30° C., 0.25 vvm, and 350 rpm for 2 days under shaking. After culture was finished, the culture was centrifuged at 8000 rpm for 20 min., to separate into a bacterial precipitate and a supernatant as a microorganism-free culture.

The supernatant was applied to an activated charcoal column, and then the cycloisomaltooligosaccharides absorbed thereon to were eluted stepwise with ethanol with the concentration increased by 5% in each elution. The largest amount of the object cyclooligosaccharides were contained in the fraction eluted with 20% ethanol. This eluate was concentrated in a rotary evaporator and then analyzed by HPLC on TSK gel Amide 80 column (a partition-adsorption chromatography column produced by Tohso Co., Ltd.). The result is set forth in FIG. 3A. This crude cycloisomaltooligosaccharide solution was concentrated in a rotary evaporator and then subjected to HPLC on YMC PA43 column (a preparative partition-adsorption chromatography column produced by Yamamura Kagaku Co., Ltd.), thus separating into each cycloisomaltooligosaccharide.

Figure 1A:
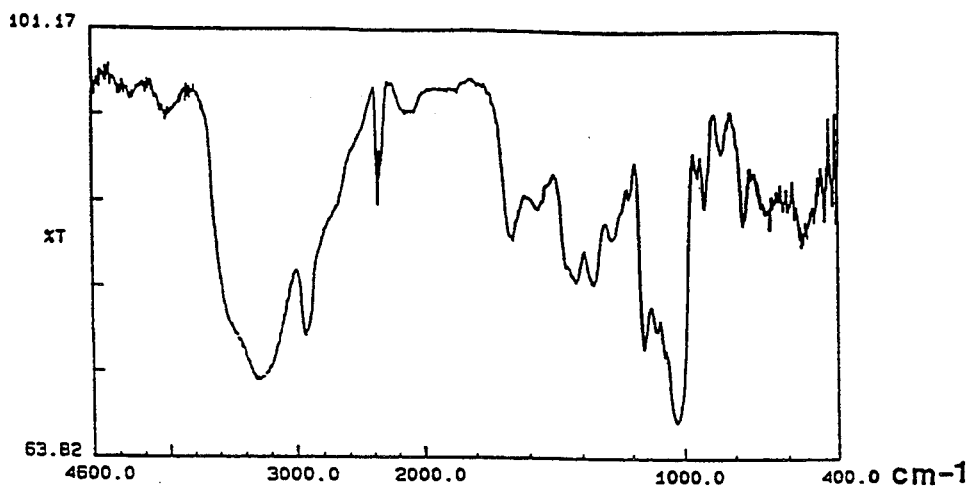
FIG. 1A shows the absorption spectrum of the cyclic heptamer of glucose.
Figure 1B:
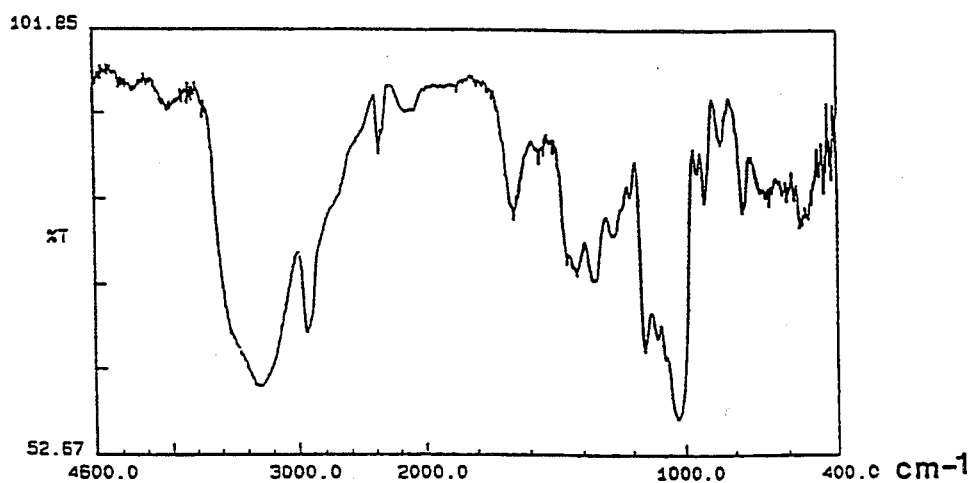
FIG. 1B shows the absorption spectrum of the cyclic octamer of glucose.
Figure 1C:
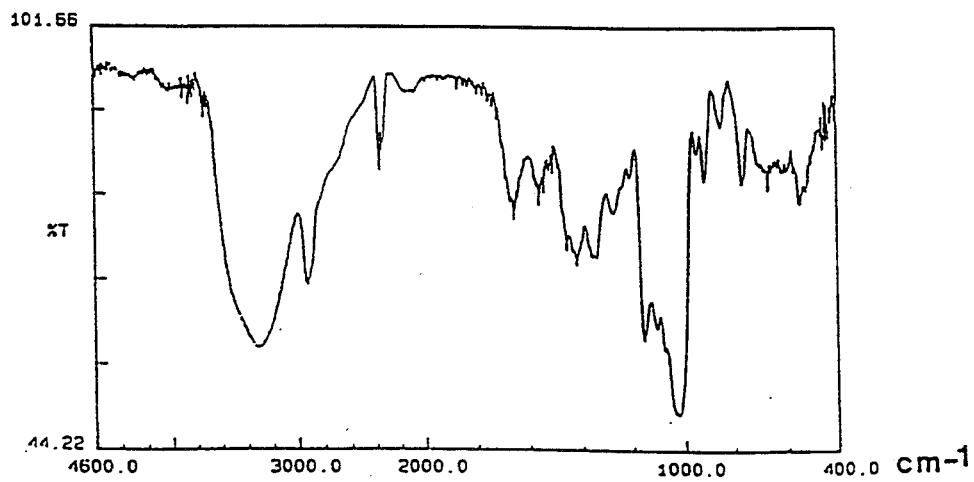
FIG. 1C shows the absorption spectrum of the cyclic nonamer of glucose.
Figure 2:
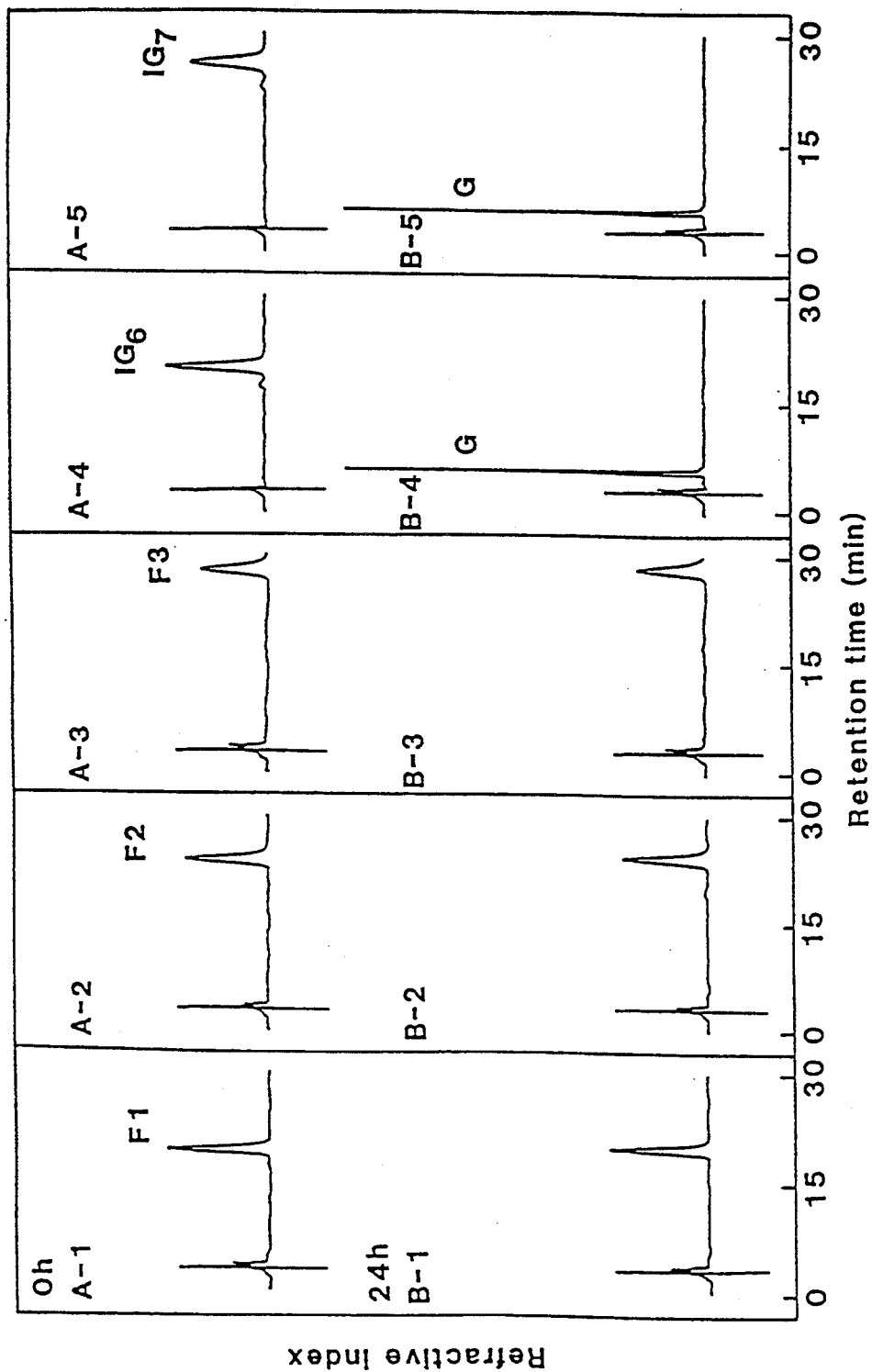
FIG. 2 shows the result of enzymatic analysis of the 3 cycloisomaltooligosaccharides of the present invention.
Figure 3:
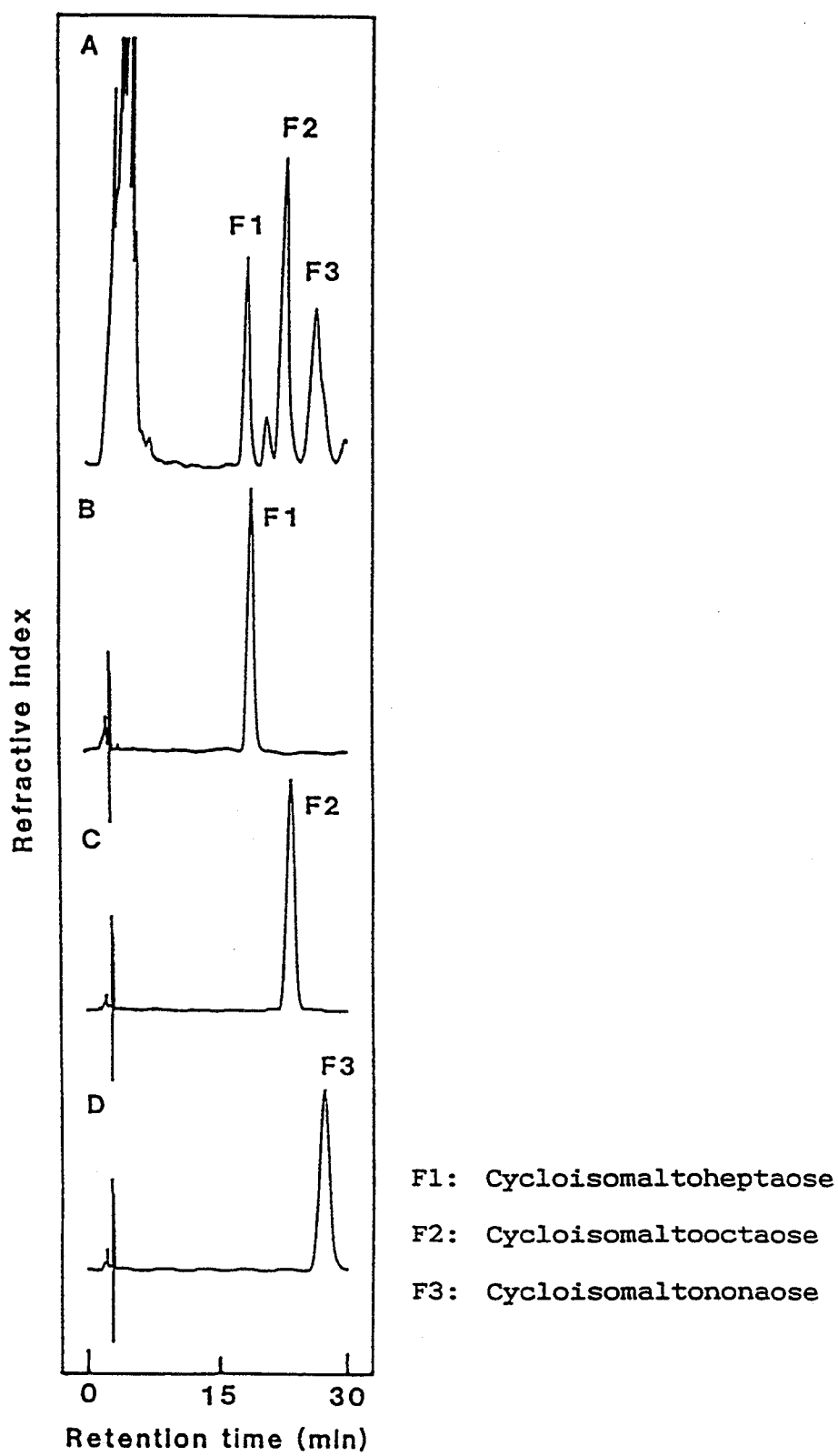
FIG. 3 shows the result of analysis in HPLC of the 3 cycloisomaltooligosaccharides of the present invention (A: an eluate in chromatography on activated charcoal, B-D: separated cycloligosaccharides).

Each fraction was concentrated with a rotary evaporator. For removal of linear isomaltooligosaccharides mixed as impurities, glucodextranase (exo-type dextranase) was added to the concentrate and the mixture was allowed to react overnight at 40° C. The reaction solution was boiled for termination of the reaction, then centrifuged for removal of the denatured proteins, and applied again to YMC PA43 column in HPLC, to separate into each cycloisomaltooligosaccharide. Each fraction was concentrated in a rotary evaporator, and the resulting concentrate was analyzed for oligosaccharide purity in HPLC on TSK gel Amide 80 column (a partition-adsorption chromatography column produced by Tohso Co., Ltd.). The result is shown in FIG. 3 B-D. A 98% or more purity was attained for each oligosaccharide. The oligosaccharide fractions were lyophilized to give about 60 mg cycloisomaltoheptaose, about 200 mg cycloisomaltooctaose and about 100 mg cycloisomaltononaose, respectively.

EXAMPLE 2

500-ml flasks, each charged with 100 ml of a liquid medium (tap water, pH 7.0) composed of 1% dextran 40 (produced by Meito Sangyo Co., Ltd.), 1% peptone (Kyokuto Seiyaku Kogyo Co., Ltd.), 0.5% NaCl and 0.1% yeast extract (produced by Difco), were sterilized at 120° C. for 20 min. The bacterial strain, *Bacillus* sp. T-3040 (FERM BP-4132), was inoculated onto the medium and cultured at 30° C. for 1 day under shaking.

1000 ml of the culture thus obtained was inoculated onto 300 l medium in a 500 l tank with the same medium composition sterilized under the same conditions as above, and the microorganism was aerobically cultured for 3 days under shaking at 30° C., 0.25 wm, and 70 rpm. After the culture was finished, the microorganism was removed from 300 l of the culture solution through ultrafiltration membrane Microza ® produced by Asahi Kasei Co., Ltd.), and the microorganism-free culture was concentrated to 6.3 l of liquid through a hollow fiber membrane (cut off molecular weight>6000), and the resulting concentrate was divided into 900-ml aliquots and stored −20° C.

900 ml of the concentrate was used for purification of cycloisomaltooligosaccharide synthase. The concentrate was thawed and then dialyzed overnight at 4° C. against 10 mM phosphate buffer, pH 7.0, containing 1 mM EDTA. The dialyzate was centrifuged for removal of insolubles, and the supernatant was applied to DEAE-Sepharose CL6B column pre-equilibrated with the same buffer. After washed with the same buffer, the absorbed protein was eluted with 0-0.8M linear gradient of NaCl. The fractions with the enzyme activity, 320 ml, were combined, and ammonium sulfate was added at a final concentration of 1M. Then, insolubles were removed by centrifugation and the supernatant was purified by preparative HPLC in the manner as described below. The supernatant was applied to TSK gel Phenyl 5PW column pre-equilibrated with 100 mM phosphate buffer, pH 7.0, containing 1.0M ammonium sulfate and 10 mM EDTA, followed by washing with the same buffer. The adsorbed protein was eluted with 1.0-0M linear gradient of ammonium sulfate.

The fractions (150 ml) with the enzyme activity were combined, followed by addition of ammonium sulfate to a final concentration of 1.0M thereto. Insolubles were removed by centrifugation, and the supernatant was applied again to TSK gel Phenyl 5PW column pre-equilibrated with 100 mM phosphate buffer, pH 7.0, containing 1.0M ammonium sulfate and 10 mM EDTA. The column was then washed with the same buffer and washed once with the same buffer with the ionic strength of ammonium sulfate lowered to 0.3M, and the adsorbed protein was eluted with 0.3-0M linear gradient of ammonium sulfate.

The fractions with the enzyme activity, 88 ml, were collected and concentrated into about 1 ml liquid which in turn was diluted with 20 ml of 10 mM phosphate buffer, pH 7.0, containing 1 mM EDTA. This solution was applied to TSK gel DEAE 5PW column pre-equilibrated with 10mM phosphate buffer, pH 7.0, containing 1 mM EDTA, then washed with the same buffer, and washed once with 0.15 M NaCl. The absorbed protein was eluted with 0.15-0.4 M linear gradient of NaCl.

The fractions with the enzyme activity, 12 ml, were collected and concentrated to 0.9 ml liquid by ultrafiltration. 0.3 ml aliquot of the resultant enzyme concentrate was applied to TSK gel G3000SW column pre-equilibrated with 100 mM phosphate buffer, pH 7.0, containing 10 mM EDTA and 200 mM NaCl, and was then eluted with the same buffer. The remaining enzyme concentrate, 0.6 ml, was divided into 0.3-ml aliquots, and each aliquot was applied to the column in the same manner as described above. The fractions with the enzyme activity were collected and analyzed by SDS-PAGE. The result showed one single band, indicating that the sample is free from any impurities.

The purified cycloisomaltooligosaccharide synthase, 12 mg, was obtained in the above procedure. The physicochemical properties of the present purified enzyme were as set forth above. It was confirmed that dextran incubated with the present purified enzyme forms cycloisomaltooligosaccharides.

EXAMPLE 3

300 l liquid culture of Bacillus sp. T-3040 was passed through a Microza® membrane for removal of the microorganism, and the microorganism-free culture was concentrated to 6.3 l liquid through a hollow fiber membrane (cut off molecular weight>6000), and was then divided into aliquots each 900 ml for storage at −20° C. A part of the culture concentrate was mixed with 10 l aqueous solution of 100 g dextran (produced by Meito Sangyo Co. Ltd.) in 10 mM phosphate buffer, pH 6.5, and the mixture was incubated for 48 hours at 40° C. The solution was boiled for termination of the reaction, with activated charcoal added for adsorption of unreacted dextran. After removal of the activated charcoal, the supernatant was applied to an activated charcoal column pre-equilibrated with deionized water and was then washed with deionized water. The adsorbed oligosaccharides were eluted with a linear gradient of ethanol. Cyclooligosaccharide fractions were combined, then concentrated, and applied to an ODS column pre-equilibrated with deionized water. After washed with deionized water, the oligosaccharides were eluted with a linear gradient of ethanol, and fractions of each oligosaccharide were combined and lyophilized.

Figure 4:
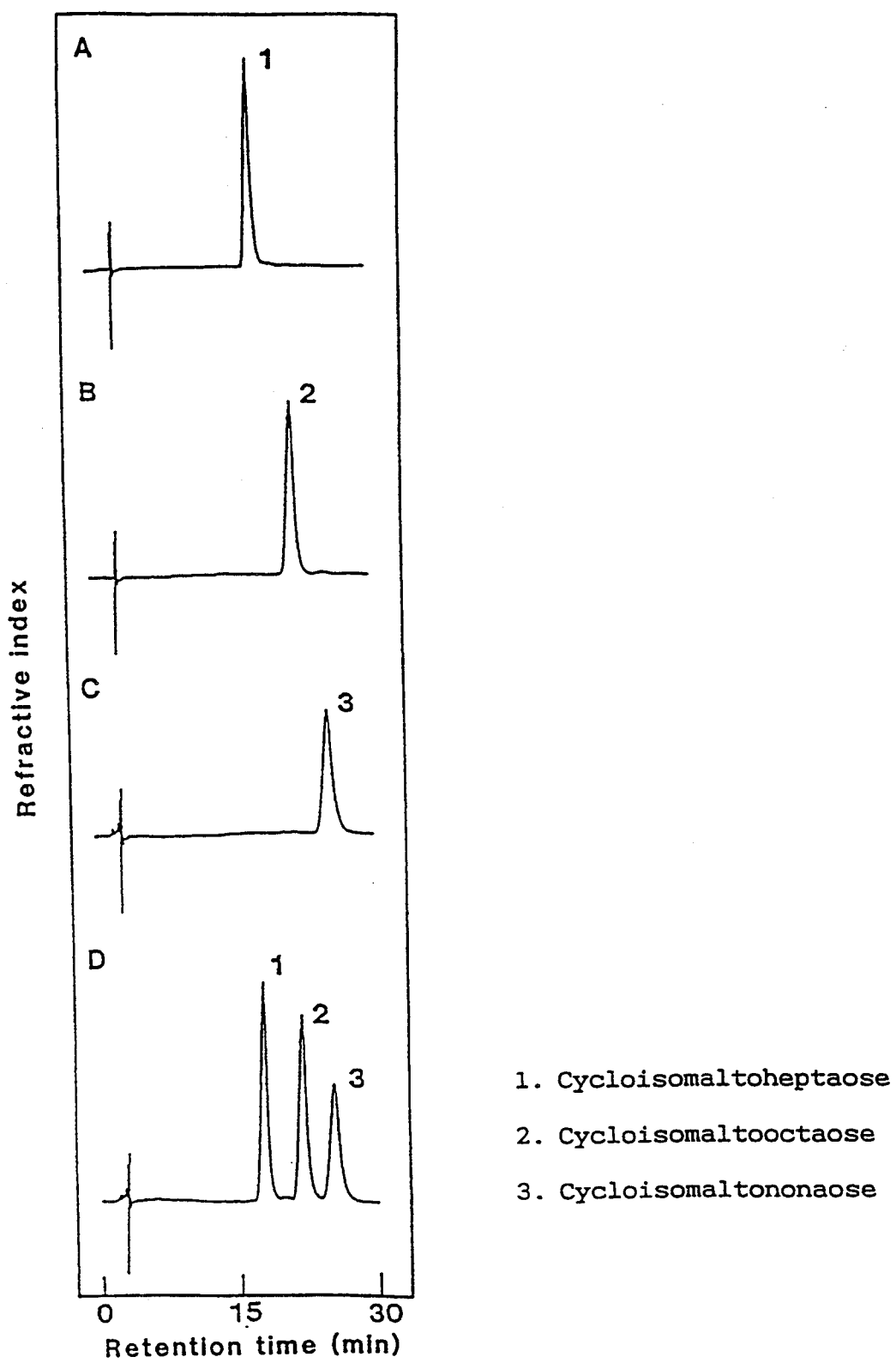
FIG. 4 shows profiles in HPLC of the cycloisomaltooligosaccharides of the present invention.

The weights of the resulting cycloisomaltooligosaccharides are 2.1 g cycloisomaltoheptaose, 4.6 g cycloisomaltooctaose, and 1.0 g cycloisomaltononaose. The yield of the cycloisomaltooligosaccharides in total was 7.7%. HPLC analysis indicated that the purity of each oligosaccharide was 98% or more. FIG. 4 shows profiles in HPLC of the cycloisomaltooligosaccharides.

HPLC analysis was conducted on TSK gel Amide (a partition-adsorption chromatography column produced by Tohso Co., Ltd.). In FIG. 4, A is the cycloisomaltoheptaose fraction; B the cycloisomaltooctaose fraction; C the cycloisomaltononaose fraction; and D the standard.

What is claimed is:

1. A cycloisomaltooligosaccharide having glucose residues in α-1,6 linkage represented by formula I:

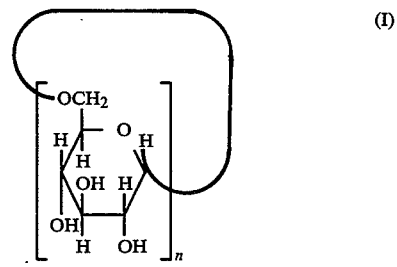

wherein n stands for an integer of 7-9.

2. The cycloisomaltooligosaccharide according to claim 1, wherein n is 7.

3. The cycloisomaltooligosaccharide according to claim 1, wherein n is 8.

4. The cycloisomaltooligosaccharide according to claim 1, wherein n is 9.

* * * * *